United States Patent
Kuehn et al.

(10) Patent No.: US 7,953,208 B2
(45) Date of Patent: May 31, 2011

(54) X-RAY RADIATION DIAPHRAGM AND CONTROL METHOD THEREFOR, AND CT DEVICE EMBODYING SAME

(75) Inventors: Ulrich Kuehn, Baiersdorf (DE); Heiko Wolf, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 111 days.

(21) Appl. No.: 12/143,287

(22) Filed: Jun. 20, 2008

(65) Prior Publication Data

US 2008/0317212 A1 Dec. 25, 2008

(30) Foreign Application Priority Data

Jun. 22, 2007 (DE) .......................... 10 2007 028 902

(51) Int. Cl.
*G21K 1/04* (2006.01)
(52) U.S. Cl. .......................... 378/151; 378/146; 378/150
(58) Field of Classification Search .................. 378/147, 378/148, 150, 151, 146
See application file for complete search history.

(56) References Cited

U.S. PATENT DOCUMENTS

| | | | | |
|---|---|---|---|---|
| 5,165,106 A | * | 11/1992 | Barthelmes et al. | 378/150 |
| 5,396,534 A | * | 3/1995 | Thomas | 378/147 |
| 5,757,881 A | | 5/1998 | Hughes | |
| 6,459,769 B1 | | 10/2002 | Cosman | |
| 6,760,402 B2 | * | 7/2004 | Ghelmansarai | 378/65 |
| 6,999,556 B2 | * | 2/2006 | Nakano | 378/152 |
| 2003/0112924 A1 | | 6/2003 | Seufert | |
| 2006/0039536 A1 | | 2/2006 | Nishide et al. | |
| 2007/0297565 A1 | * | 12/2007 | Wofford et al. | 378/65 |

* cited by examiner

*Primary Examiner* — Chih-Cheng G Kao
(74) *Attorney, Agent, or Firm* — Schiff Hardin LLP

(57) ABSTRACT

A collimator device has at least one masking device that is adjustable between two end positions for collimation of a beam fan in an x-ray CT device, wherein the x-ray fan is schematically not masked in a first end position. The x-ray beam is more than half-masked in a second end position of the masking device. In a method for operation of such a collimator device as well as an x-ray CT device for examination of a subject having an x-ray source, a collimator device, and a control device for regulation of the aperture width of the masking device, an x-ray detector is arranged opposite the x-ray source and the collimator device and that detects the x-rays modified due to the intervening examination subject; and an image construction device reconstructs an image of the examination subject therefrom.

12 Claims, 3 Drawing Sheets

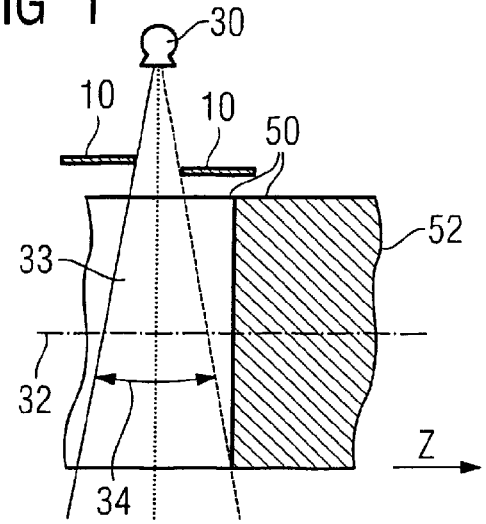
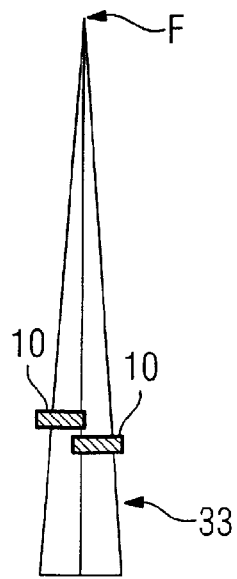
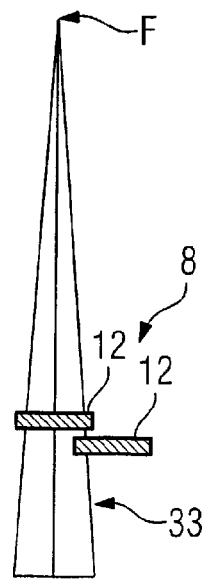
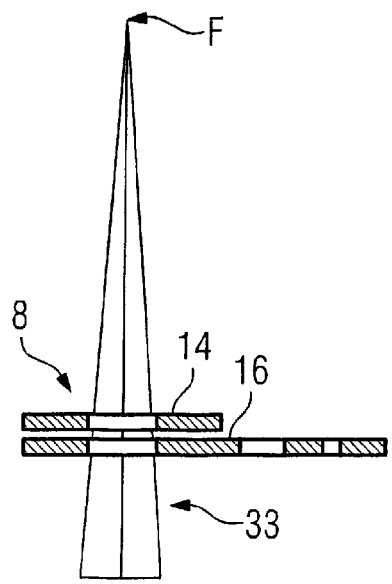

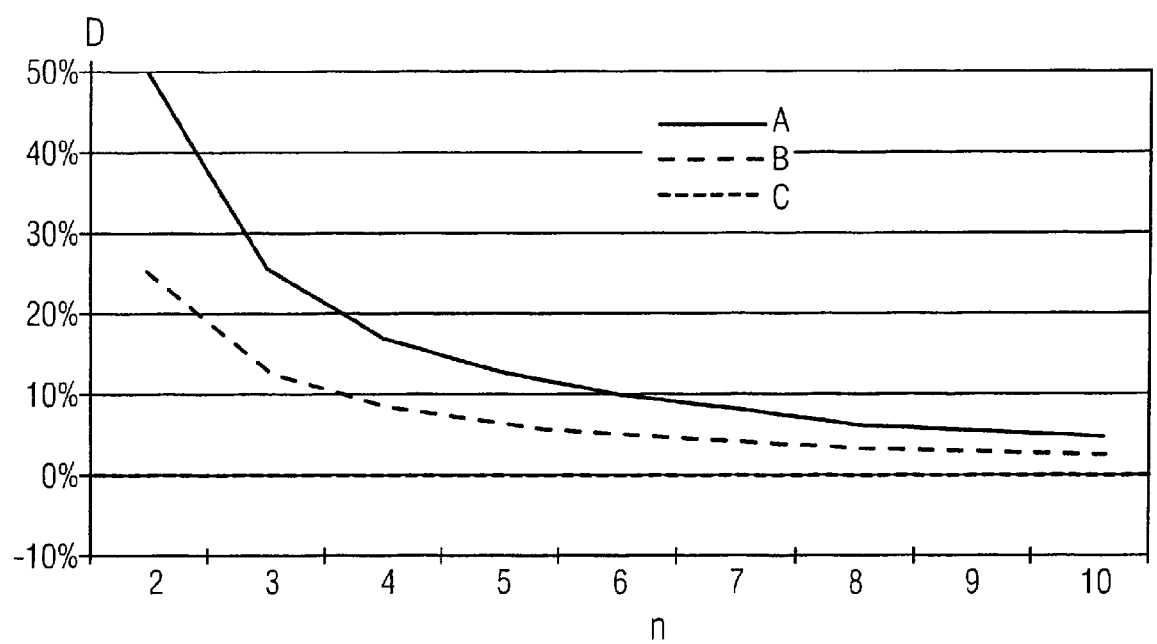

X-RAY RADIATION DIAPHRAGM AND CONTROL METHOD THEREFOR, AND CT DEVICE EMBODYING SAME

BACKGROUND OF THE INVENTION

1. Field of the Invention

The present invention concerns a radiator diaphragm, i.e., a device for collimation of x-rays of the type having at least one masking element that is adjustable between two end positions. Furthermore, the invention concerns a method to control this radiator diaphragm or collimator device and an x-ray CT device embodying such a radiator diaphragm or collimator device according to the invention.

2. Description of the Prior Art

Collimation is the procedure for directing light beams or x-rays to propagate in a parallel manner. A lens that directs the light of a punctiform (in terms of its focal point) light source parallel to the optical axis of the lens is used for collimation of light rays. This parallel beam can be used as a replacement for a light source at infinite distance. Diaphragm devices (known as radiator diaphragms) are typically used for collimation or of x-rays in CT apparatuses (computed tomography apparatuses). Many variants and processes are hereby known.

The x-ray fans (can beams) are gated in a direction that is usually designated as the z-direction by the collimation, so that only the rays that can be evaluated by the acquisition system (DMS—data measurement system) irradiate the patient. This is intended to prevent the patient from being exposed to a higher radiation dose in the examination that would be absolutely necessary. The reason for this is in that the employed x-rays can cause mutations in a living organism. In principle it should be ensured that only the minimum possible radiation dose is used.

The collimation width of a slot through which the generated x-rays pass is adjusted before beginning an examination of a subject known as the "scan". The collimation width remains constant during the "scan". This means that the slot produced by adjustment in the diaphragm must generally be displaced in the z-direction in order to compensate for position changes of the focus, for example due to thermal (heating) effects.

The principles of z-collimation or gating are presented in the following. Two prevalent methods have conventionally been used in order to collimate the beam fans in the z-direction. In the first method two individually movable diaphragm jaws or plates are used that are mechanically or electronically coupled with one another. In this variant the electromechanical effort is relatively high. In contrast to this, a high flexibility in the adjustment of desired or required collimation width is advantageous. A z-regulation to compensate for thermal effects is possible without problems. The second method uses a movable plate with multiple slots of different widths. The collimator widths are thus predetermined in a fixed manner by the slot widths. In comparison to the first cited method, the electromechanical effort is very slight. A z-regulation for compensation of thermal effects is likewise possible.

Furthermore, radiator diaphragms can be differentiated between static and dynamic collimation. In static collimation, the adjustment ensues at the beginning of the examination and is not changed or adapted in the course of the examination. The patient is thereby subjected to an unnecessary beam exposure at the beginning or at the end of the scan, since not all measurement data can be reconstructed in a manner that is effective for the image. In dynamic collimation, the beam diaphragms are dynamically regulated. In order to not reduce the dose used for the scan and acquisition process at the beginning and end of a spiral scan, the radiator diaphragm can dynamically gate or mask the scan process.

In radiator diaphragms with diaphragm jaws, the individual diaphragm jaws conventionally are able to respectively mask only half of the beam fan. In United States Patent Application Publication No. 2006/0039536, a dynamic collimation is described in which each diaphragm jaw can respectively mask only half of the beam fan. In this type of collimation, a diaphragm jaw (collimator jaw) is opened or closed in the respective first or last rotation of a spiral scan. A dynamic collimation only on one side is thereby achieved, and thus in principle only one part of the unused dose is reduced. The collimation system described in that published application employs eccentric rollers as diaphragm jaws. Given the use of rollers, the space requirement for the masking region and the designed space height is increased.

By expanding the z-masking of CT apparatuses, the proportion of unused dose at the beginning and end of a spiral scan (helical scan) is significantly increased. This leads to an unnecessary radiation exposure for the patient at these points in time.

SUMMARY OF THE INVENTION

An object of the present invention is to provide a device and a method that enable the subject or the patient to be examined to minimize the effective general radiation exposure.

This object is achieved in accordance with the present invention by a collimator device, a method for collimating x-rays, and a computed tomography device embodying such a collimator device and operating according to such a method wherein at least one masking device is movable between two end positions, with the masking device substantially not masking the x-rays when in a first of the end positions and masking more than half of the x-rays when in a second of the end positions.

To the greatest possible extent, only the radiation dose effective for the image, and therefore the minimum required, is applied using the device according to the invention as well by the method according to the invention. Beam portions that are not effective for the image are largely masked and therefore kept away from the patient. This is achieved by complete collimation. A collimator device according to the invention for complete, dynamic collimation has at least one (but advantageously two) masking devices. The masking devices are such that they do not or substantially do not, mask the x-ray beam in the opened state. In the closed state, a masking device masks more than half of the x-ray beam. According to a preferred embodiment, the masking device or a respective masking device of multiple masking devices can largely mask the entire x-ray beam.

According to a further preferred embodiment, the collimator device has radiator diaphragms with two individual diaphragm jaws. The diaphragm jaws are designed such that each of these two diaphragm jaws can mask the entire beam fan. The unused dose at the start or end of a spiral scan thus can be completely avoided.

In order to be able to achieve the masking of the entire beam fan with a diaphragm jaw, both the masking region of the diaphragm jaws and their travel region must be doubled relative to the devices known from the prior art. The degree of masking is determined only by the predominating tolerances and the available dynamic of the diaphragm jaws. The advantages of the complete dynamic collimation via radiator diaphragms with two individual diaphragm jaws are on the one hand that in principle no limitation of the reduction of used dose ensues. Furthermore, in the case of a gantry-type CT apparatus, no alteration of the designed space in the direction between the radiator and the patient opening is necessary.

According to a further preferred embodiment, the dynamic collimation ensues by radiator diaphragms formed by a pre-diaphragm and a movable slot plate. The slot plate can thereby completely mask the beam. In radiator diaphragms with a movable slot plate, the dynamic collimation can be executed only in the steps in which the largest slot is utilized. One edge of the stationary pre-slot collimation is used during the dynamic collimation. This diaphragm, however, must be designed somewhat larger, since the possibility of compensating for the position changes of the focus must be provided. The degree of efficacy of the dose reduction is thus dependent on the design of the adjustment range. In comparison to the embodiment of the invention with two individual diaphragm jaws with complete masking, the embodiment with the movable slot diaphragm does not achieve the maximum possible degree of efficacy. For dynamic collimation using radiator diaphragms with a movable slot plate, the reduction of unused dose is in principle only slightly limited. Likewise, given this embodiment no alteration of the designed space is necessary in a gantry-type CT apparatus in the direction between the radiator and the patient opening.

For complete dynamic collimation, the collimator is almost completely closed in the start and/or end position of the scan process. The collimator is correspondingly opened in the course of the scan process, such that only the required patient regions are exposed.

In the collimation system the diaphragm jaws can be designed such that they can be moved linearly. In this case, linear actuators are used. This is, for example, a rotation motor with shaft, linear motor, piezomotor or another actuator known to those skilled in the art. Given these actuators an increase of the travel path can be achieved by a suitable scaling (thus not by redesign) of the system. The possible aperture area is therefore not limited by the available designed space between the radiator and the patient opening. It is thus furthermore possible to provide the travel region for the thermal Z-regulation.

Furthermore, the invention concerns a method to control such a collimator device. The aperture of the collimator is altered during the scan process, wherein this alteration can in particular ensue continuously. At the beginning of the scan process the collimator device is nearly completely closed so that only a narrow beam fan scans the subject. The opening and closing of the collimator ensues by means of a linear drive. A rotation motor with shaft, a linear motor, piezomotor or another actuator known to those skilled in the art is used. A rotary drive that interacts with rollers or camshafts or the like can also alternatively be used in the method according to the invention.

Furthermore, a control device that correspondingly adapts the aperture of the collimator is coupled to the collimator.

The collimator device according to the invention is advantageously used in an x-ray CT apparatus. An x-ray CT device for examination of subjects (in particular of patients) consists of an x-ray radiator, a collimator and associated control device, an x-ray detector and an image construction device.

In the examination, the subject is arranged such that the x-ray source and the collimator are located on the one side and the x-ray detector is located on the other side. The radiator and the oppositely-situated detector rotate around the body. For example, a multi-line x-ray detector is used as an x-ray detector. The x-ray detector detects the radiation that passes through the examined subject and was thereby altered by different degrees of absorption. The image construction device reconstructs the examined subject based on the data about the beams used and the data determined by the x-ray detector and graphically presents the information so acquired. According to a preferred embodiment, a 2D image reconstruction device is used. The aperture of the collimator is controlled by the control device.

BRIEF DESCRIPTION OF THE DRAWINGS

FIG. 1 illustrates the basic principle of a known device for complete dynamic collimation.

FIG. 2 illustrates known collimation on only one side by means of two diaphragm jaws that mask only half of the beam area.

FIG. 3 illustrates the basic principle of a device, in accordance with the invention for complete collimator by means of two diaphragm jaws that mask the entire beam area.

FIG. 4 illustrates the complete collimator in accordance with the invention in using a slot plate;

FIG. 8 shows the dose reduction dependent on the degree of masking per diaphragm jaw as well as the length of the scan.

DESCRIPTION OF THE PREFERRED EMBODIMENTS

Figure 5:
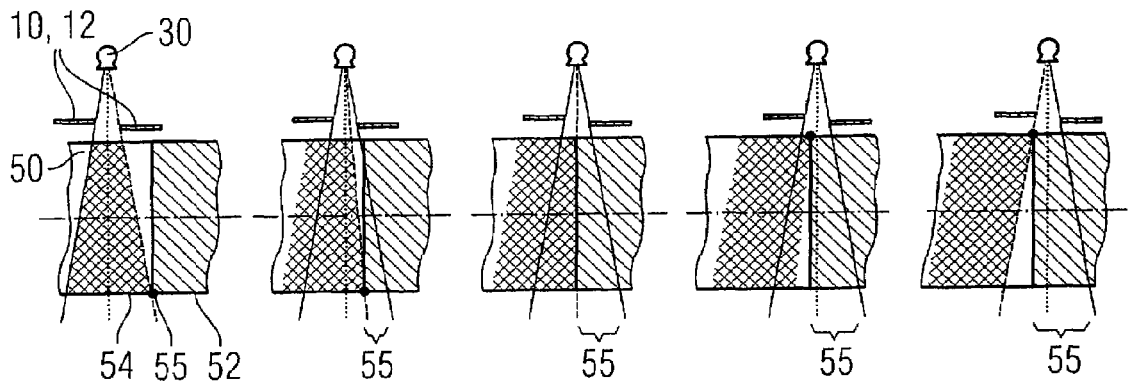
FIG. 5 shows the radiation exposure given static collimation (prior art).

One possible design of a device with dynamic collimation according to the invention is illustrated using FIGS. 3 and 4.

FIG. 1 illustrates the general known prior art. The fan beam 33 is generated by means of the x-ray tube 30. Additional scattered radiation arises in the apparatus. The beam 33 is limited in the x-direction (and therefore in the scan direction) by means of the diaphragm jaws 10 of the collimator, whereby the fan angle 34 is generated. The examination subject or the patient 50 is located in the rotation axis (z-direction) of a computed tomography apparatus 32. Furthermore, a reconstruction region 52 is shown in order to make the comprehension of FIG. 5 through 7 easier. This is the region of the patient that is examined from which data are acquired and evaluated.

FIG. 5 (prior art) shows which regions of the examination subject or of the patient 50 are exposed to the radiation given static collimation according to the variants described above (see FIG. 1). The checkered area 54 thereby represents the radiation-exposed region that is not evaluated. This region thus represents the dose that is effective for the image. In contrast to this, the area 52 that is simply hatched marks the region that should be examined. This region 52 thus must necessarily be exposed to the beam.

It can be seen that, given static collimation, only the right edge of the fan beam 55 is graphically evaluated at the beginning of the examination. The remaining beam thus does not lead to an exposure of the patient 55 in regions 54 that are not examined and reconstructed.

Figure 6:
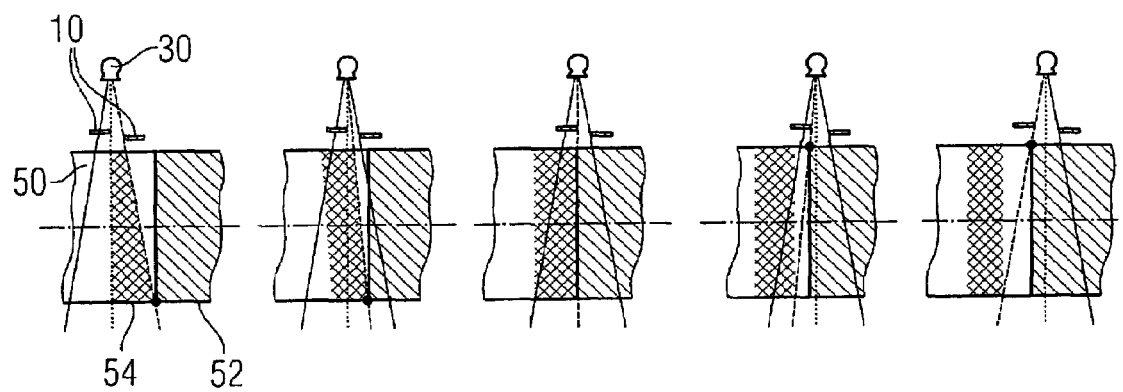
FIG. 6 shows the radiation exposure given dynamic collimation on only one side (prior art).

The principle described in United States Patent Application Publication No. 2006/0039536 of a dynamic collimation on one side in which each diaphragm jaw 10 respectively masks only half of the beam fan is shown in FIGS. 2 and 6 (prior art). A diaphragm jaw 10 is opened and closed respectively in the first and last rotations of a spiral scan. A portion of the unused dose is thereby reduced; the patient 50 is thus exposed to a lower unused radiation dose.

Figure 7:
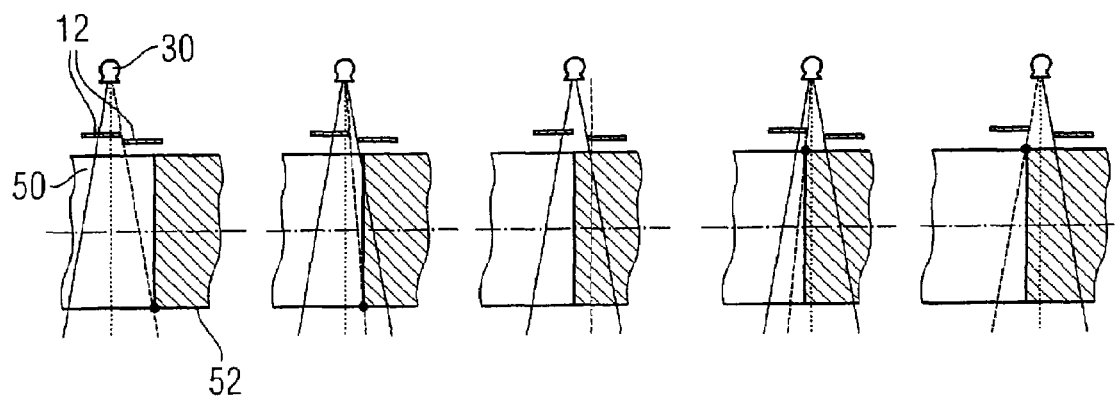
FIG. 7 shows the radiation exposure given complete dynamic collimation according to the present invention.

Exemplary embodiments for the complete collimation according to the invention are shown in FIGS. 3, 4 and 7.

FIG. 3 shows a preferred embodiment in which the screening of the beam ensues with two individual diaphragm jaws 12. The device for collimation is generally designated as a masking device 8 in the present context. The diaphragm jaws 12 are thereby designed such that each of these two diaphragm jaws 12 masks the entire beam fan. As shown in FIG. 7, the unused dose at the start or end of a spiral scan can be completely avoided since the two collimators can be brought into a position in which the radiation is not passed. The collimators are slightly opened in order to acquire the first region 52 to be examined. The shielding effectiveness of this device is thereby determined only by the prevalent tolerances and the available dynamic of the diaphragm jaws 12.

Both the masking region of the diaphragm jaws 12 and their travel range must be doubled in order to be able to achieve the masking of the entire beam fan with one diaphragm jaw 12.

FIG. 4 shows a preferred embodiment in which the complete dynamic collimation ensues with a masking device 8 in the form of a pre-diaphragm 14 in connection with a movable slot plate 16. The dynamic collimation utilizes the largest slot. For dynamic collimation, one edge of the stationary pre-slot collimation is used as well. This diaphragm must be designed large so that position changes of the focus can be compensated. The effectiveness of the dose reduction is thus dependent on the design of the adjustment range. The dose adjustment in this embodiment does not achieve the maximum value as is the case [with] the two individual diaphragm jaws 12 with complete masking (see FIG. 3).

FIG. 8 compares the reduction of the unneeded radiation dose of the different collimation methods for the patient. Given static collimation (see also FIG. 5) the patient is exposed to a significant radiation dose that is not graphically evaluated. Due to the static setting of the diaphragm jaws 10, the additional radiation dose is maximal and is not minimized in the course of the examination (dashed line C, continuously at 0% dose reduction).

Given a scan length of two total collimations (n=2), by means of dynamic collimation (dashed line B) on one side with diaphragm jaws 10 that can mask half of the x-ray beam (shown in FIGS. 2 and 6), the dose of non-imaging radiation is reduced by approximately 25% in comparison to static collimation. The additional radiation dose (what is known as the unused radiation dose) for the patient is also reduced given longer scans (n>2). The reduction in comparison to static collimation is approximately 12% given a scan length of n=4, approximately 5% given n=6 and approximately 3% given n=10.

The presentation clearly shows that the dose of non-imaging radiation can be further reduced by means of complete dynamic collimation (solid line A) according to the invention. The reduction in comparison to static collimation is approximately 50% given n=2, approximately 17% given n=4, approximately 10% given n=6 and approximately 5% given n=10. The advantage primarily results given relatively short scans, what are known as spiral scans (n$\leq$5).

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for collimating an x-ray beam comprising the steps of:

mounting a diaphragm with a fixed aperture opening therein in a path of x-rays, and movably mounting a slotted plate comprised at least partially of material that is impermeable to x-rays and having a slot therein, to allow said slotted plate to be moved between two end positions relative to said path and relative to said fixed aperture opening to collimate said x-rays to form an x-ray beam;

configuring said two end positions and said slotted plate to cause said fixed aperture opening and said slot to overlap to produce substantially no masking of said x-rays when said slotted plate is in a first of said end positions, and to mask all of said x-rays, by said fixed aperture opening and said slot not overlapping, when said slotted plate is in a second of said end positions, with said fixed aperture opening and said slot defining an adjustable aperture for passage of said x-rays as said slotted plate is moved between said two end positions;

conducting a scan of a subject with said x-rays to obtain x-ray image data from a predetermined region of the subject; and automatically controlling movement of said slotted plate to automatically adjust said adjustable aperture during said scan to minimize exposure of the subject to said x-rays by substantially confining irradiation of the subject with said x-rays to said region.

2. A method as claimed in claim 1 comprising continuously adjusting movement of said slotted plate, and thereby continuously adjusting said adjustable aperture, during said scan.

3. A method as claimed in claim 2 comprising positioning said slotted plate to substantially close said adjustable aperture at a beginning of said scan, to allow only a narrow x-ray beam to irradiate the subject.

4. A controlled collimator arrangement for collimating x-rays, comprising:

a device housing, a radiation masking device comprising a radiation diaphragm having a fixed aperture opening therein, and a slotted plate movably mounted in said device housing for adjustment between two end positions in said device housing relative to said fixed aperture opening, said slotted plate being comprised of material that is impermeable to x-rays and having a slot therein, and said two end positions and said slotted plate being configured to cause said fixed aperture opening and said slot to overlap to produce substantially no masking of said x-rays when said slotted plate is in a first of said end positions, and to mask all of said x-rays, by said fixed aperture opening and slot not overlapping, when said slotted plate is in a second of said end positions, and said fixed aperture opening and said slot defining an adjustable aperture for passage of said x-rays as said slotted plate is moved between said two end positions; and a control device that operates said radiation masking device during a scan of a subject with said x-rays to obtain x-ray image data from a predetermined region of the subject, by automatically controlling movement of said slotted plate to automatically adjust said adjustable aperture during said scan to minimize exposure of the subject to said x-rays by substantially confining irradiation of the subject with said x-rays to said region.

5. An x-ray computed tomography device comprising:

an x-ray source that emits x-rays;

a device housing, a radiation masking device comprising a radiation diaphragm having a fixed aperture opening therein and a slotted plate movably mounted in said device housing for adjustment between two end positions in said device housing relative to said fixed aperture opening, said slotted plate being comprised of material that is impermeable to said x-rays and having a slot therein, and said two end positions and said slotted plate being configured to cause said fixed aperture opening and said slot to overlap to produce substantially no masking of said x-rays when said slotted plate is in a first of said end positions, and to mask all of said x-rays, by said fixed aperture opening and slot not overlapping, when said slotted plate is in a second of said end positions, and said fixed aperture opening and said slot defining an adjustable aperture for passage of said x-rays as said slotted plate is moved between said two end positions;

an x-ray detector located in a path of said x-rays, said x-ray source and said x-ray detector being configured to irradiate a region of a subject therebetween with said x-rays in a scan of said subject, and said x-ray detector generating x-ray image data representing attenuation of the x-rays by said subject;

a control device that operates said radiation masking device during said scan of the subject with said x-rays to obtain x-ray image data from a predetermined region of the subject, by automatically controlling movement of said slotted plate to automatically adjust said adjustable aperture during said scan to minimize exposure of the subject to said x-rays by substantially confining irradiation of the subject with said x-rays to said region; and an image reconstruction device supplied with said image data that reconstructs an image of said region of said subject from said image data.

6. An x-ray computed tomography device as claimed in claim 5 wherein said control device controls movement of said slotted plate to substantially close said adjustable aperture at at least one of a start of said scan and an end of said scan.

7. An x-ray computed tomography device as claimed in claim 5 wherein said x-ray detector is a multi-line x-ray detector.

8. An x-ray computed tomography device as claimed in claim 5 wherein said x-ray detector is a planar x-ray detector.

9. An x-ray computed tomography device as claimed in claim 5 wherein said image reconstruction device is a 3D image reconstruction device.

10. A collimator device for collimating x-rays, said collimator device comprising:
  a device housing;
  a radiation masking device comprising a radiation diaphragm having a fixed aperture opening therein, and a slotted plate movably mounted in said device housing for adjustment between two end positions in said device housing relative to said fixed aperture opening, said slotted plate being comprised of material that is impermeable to x-rays and having a slot therein; and
  said two end positions and said slotted plate being configured to cause said fixed aperture opening and said slot to overlap to produce substantially no masking of said x-rays when said slotted plate is in a first of said end positions, and to mask all of said x-rays, by said fixed aperture opening and slot not overlapping, when said slotted plate is in a second of said end positions, and said fixed aperture opening and said slot defining an adjustable aperture for passage of said x-rays as said slotted plate is moved between said two end positions.

11. A collimator device as claimed in claim 10 comprising a linear actuator that moves said slotted plate between said two end positions in said device housing.

12. A collimator device as claimed in claim 11 wherein said linear actuator is a motor selected from the group consisting of a rotary motor having a shaft, a linear motor, and a piezo-motor.

* * * * *